United States Patent [19]
Abramson

[11] 4,161,179
[45] Jul. 17, 1979

[54] VACUUM BAG FOR WOUND DRAINAGE

[75] Inventor: Harvey J. Abramson, New York, N.Y.

[73] Assignee: Metatech Corporation, Northbrook, Ill.

[21] Appl. No.: 822,564

[22] Filed: Aug. 8, 1977

[51] Int. Cl.² ............................................. A61M 1/00
[52] U.S. Cl. ............................. 128/278; 128/DIG. 24
[58] Field of Search .......................... 128/276–278, 128/145.7, 349, 2 F, 230–232, 191 R, 145.6; 141/65, 59, 316, 390; 417/470, 472–474, 343, 437; 222/206, 209; 215/5; 150/10

[56] References Cited

U.S. PATENT DOCUMENTS

| | | | |
|---|---|---|---|
| 3,372,975 | 3/1968 | Johnson | 401/183 |
| 3,572,340 | 3/1971 | Lloyd et al. | 128/278 |
| 3,752,158 | 8/1973 | Kariher | 128/278 |
| 3,780,732 | 12/1973 | Leibinsoh | 128/214 F |

FOREIGN PATENT DOCUMENTS

1194540  6/1965  Fed. Rep. of Germany ............. 150/10

*Primary Examiner*—Robert W. Michell
*Assistant Examiner*—Arthur S. Rose
*Attorney, Agent, or Firm*—Leydig, Voit, Osann, Mayer & Holt, Ltd.

[57] ABSTRACT

A vacuum bag assembly for wound drainage which utilizes a bag of thin flexible plastic in the form of an initially flat sealed envelope having opposed walls with sealed side edges and end edges and having a sealed catheter to provide communication. Vacuum is created by a pair of springs spaced along the axis of the bag with each spring being in the form of a pair of leaf spring elements lying back-to-back with their ends in register with one another and extending from one side edge of the bag to the other, the leaf spring elements being pre-stressed for bowing mutually outwardly away from the central axis. Relatively stiff flexible sheets are interposed between the springs and the walls of the bag so that upon bowing of the springs the walls of the bag are bowed outwardly uniformly over the major portion of the length thereof into distended pillow shape for development of vacuum at the catheter connection. The flexible sheets extend substantially to the side edges but are inwardly offset from the end edges so that expansion of the bag is unrestricted.

8 Claims, 11 Drawing Figures

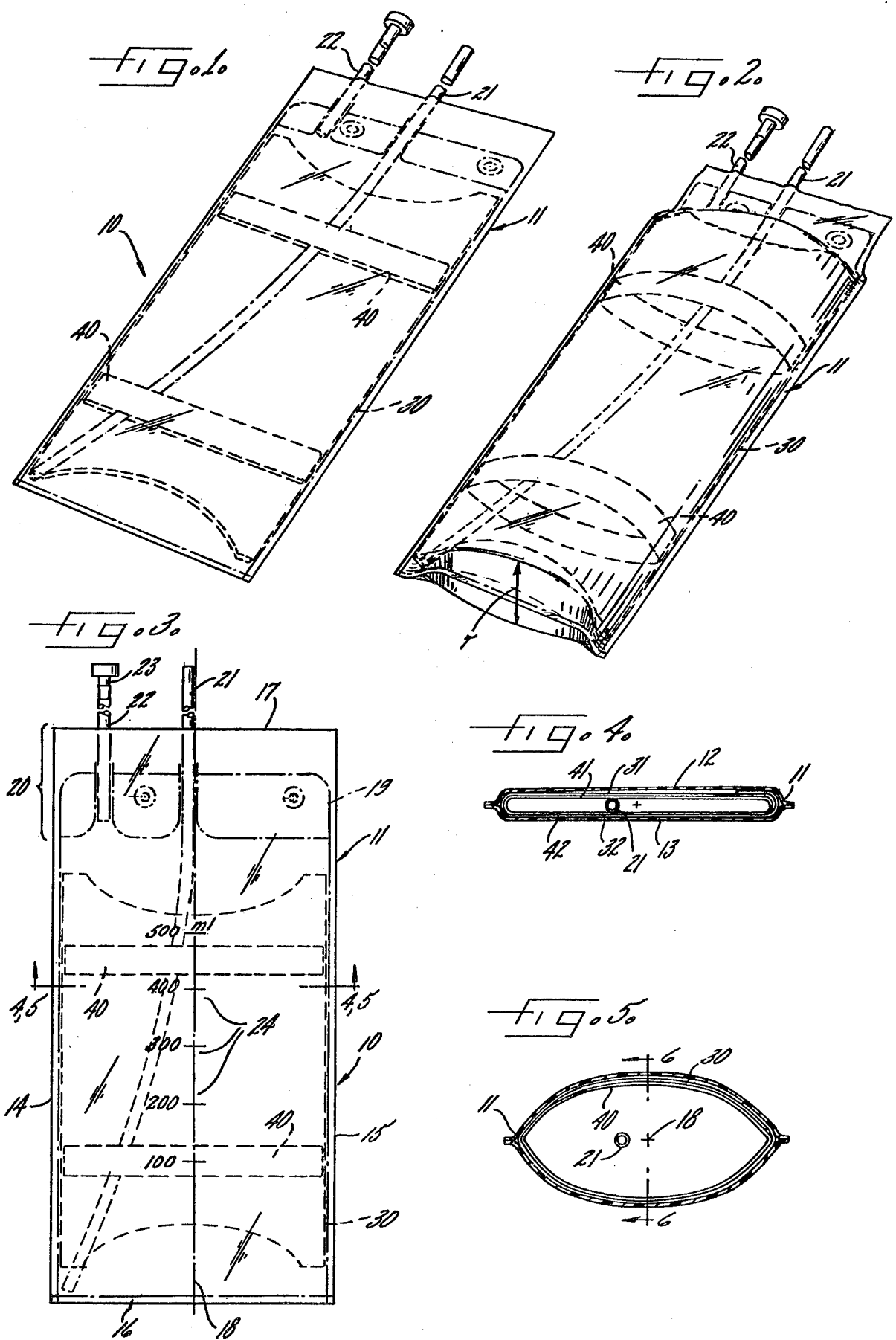

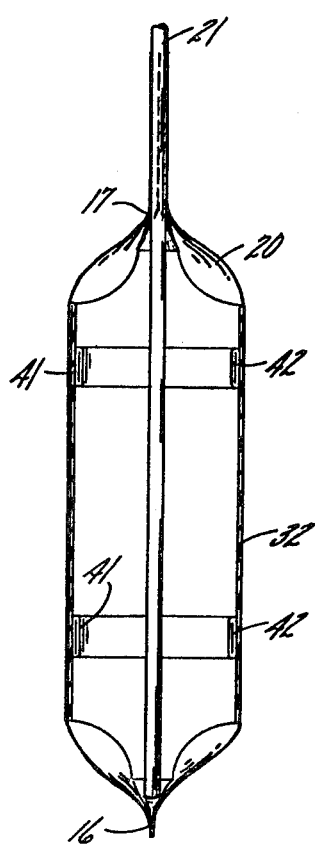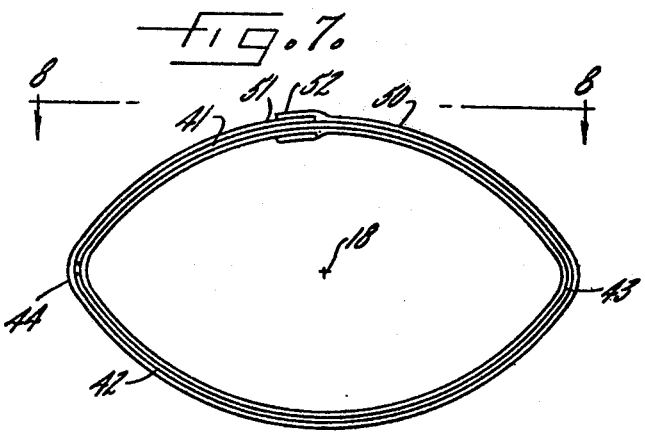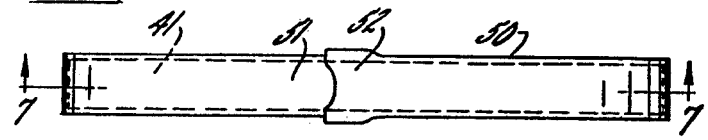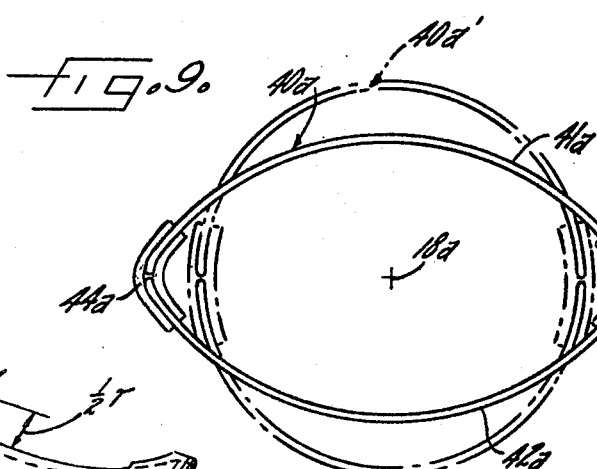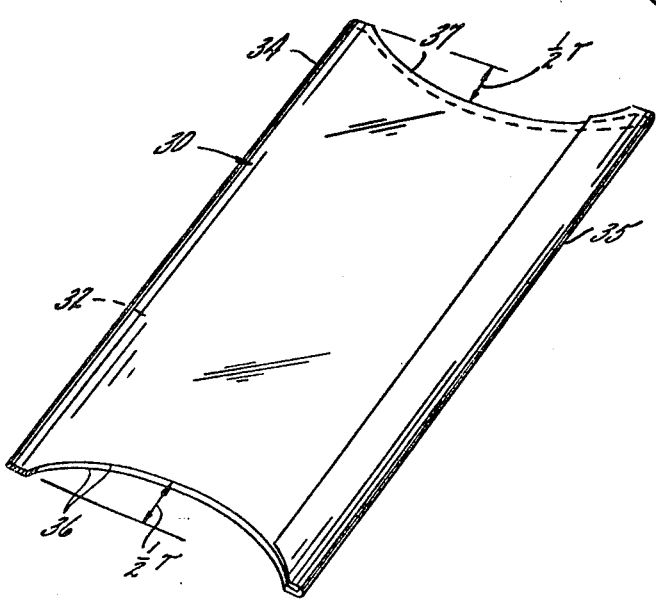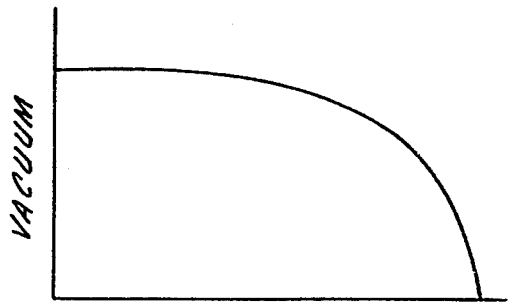

VACUUM BAG FOR WOUND DRAINAGE

DESCRIPTION OF THE INVENTION

It is an object of the present invention to provide a vacuum bag assembly for wound drainage which exerts a more constant vacuum over the evacuation cycle. It is another object of the present invention to provide a vacuum bag assembly which is more reliable than conventional devices and which substantially insures against leakage or loss of vacuum during the course of use. It is still another object of the present invention to provide a vacuum bag which is more efficient than conventional devices and which has a drainage capacity which is more nearly equal to the volume of the device in its expanded state.

It is another object of the invention to provide a wound drainage bag which is easy and convenient to use, which may be easily and precisely monitored, and which may be quickly emptied and reset when full.

It is still another object to provide a wound drainage bag which is compact, expanding into an easily handled pillow shape, which is highly economical to produce, and which may be considered disposable or capable of indefinite reusage without loss of function or reliability.

Other objects and advantages of the invention will become apparent upon reading the attached detailed description and upon reference to the drawings in which:

FIG. 1 is a perspective view of a vacuum bag assembly constructed in accordance with the present invention in its initial flat state.

FIG. 2 is a view similar to FIG. 1 but showing the device in its filled or expanded state.

FIG. 3 is a face view of the device in the flat condition.

FIGS. 4 and 5 are cross-sectional views of the device in the flat and expanded states, respectively, taken along line 4,5—4,5 in FIG. 3.

FIG. 6 is a longitudinal section of the device in its expanded state taken along line 6—6 in FIG. 5.

FIG. 7 is a detail showing the cross-section of one of the springs looking along line 7—7 in FIG. 8.

FIG. 8 is a top view of the spring of FIG. 7 looking along line 8—8 in that figure.

FIG. 9 is a view similar to FIG. 7 but showing an alternate form of spring.

FIG. 10 is a perspective showing the relatively stiff reinforcement sleeve which is interposed between the springs and the bag itself.

FIG. 11 illustrates a typical vacuum characteristic attainable with the present device.

While the invention has been described in connection with certain preferred embodiments, it will be understood that I do not intend to be limited to the particular embodiments shown but intend, on the contrary, to cover the various alternative and equivalent forms of the invention included within the spirit and scope of the appended claims.

Turning now to the drawings there is shown a vacuum bag assembly 10 which includes an outer bag 11 which is initially of flat "envelope" shape having opposed walls 12, 13, side edges 14, 15, and end edges 16, 17, the side edges defining a central axis 18. The bag is preferably formed of thin vinyl plastic of about 10 mils, heat-sealed along the dot-dash lines 19. The end edge 17 is preferably extended to form a "header" 20 providing a catheter connection 21 which communicates with the interior of the bag, leading preferably to one corner thereof, and a vent connection 22 which is fitted with a stopper 23, the connection 22 being useable for initial venting of air or for emptying the bag when it has become filled.

The connections 21, 22 are preferably integral with catheter and drain tubes, preferably vinyl, which may extend up to several feet in length. The wall 12 of the bag preferably includes volumetric calibrations as indicated at 24.

In accordance with the present invention the walls of the bag have reinforcement in the form of relatively stiff flexible sheets with at least one spring interposed between the sheets and pre-stressed outwardly for bowing of the sheets and hence the walls of the bag mutually outwardly into distended pillow shape for development of a vacuum at the catheter connection, the sheets extending substantially to the side edges but offset inwardly from the end edges of the bag to provide "area" support while accommodating the outward bowing.

The relatively stiff reinforcing sheets, indicated respectively at 31, 32 are preferably integrated into a sleeve 30 of flat, generally rectangular configuration (see FIG. 10) having side edges 34, 35 and end edges 36, 37, the end edges being arcuately scalloped, or relieved, as shown so as to leave the ends of the bag "loose" so as not to interfere with the free expansion of the device into its filled condition. The amount of inward offset is preferably $\frac{1}{2}$T, where T is the final thickness (FIG. 2).

For the purpose of bowingly expanding the reinforcing sheets, and hence the bag, springs 40 are used (FIG. 7). Each spring 40 is made up of a pair of flat leaf spring elements 41, 42 which are pre-stressed, i.e., they both tend to assume a condition in which they are bowed arcuately outward with respect to the central axis 18.

Preferably the spring elements 41, 42 are formed integrally with one another, that is, they comprise a single continuous loop. Alternatively the spring may be formed of a single continuous strip of leaf spring material centrally bent to provide a hinge 43 between them and with free ends being held in register to form a second hinge 44.

For enclosing spring 40 and for holding the free ends of the spring elements in register with one another, the spring is totally enclosed (FIG. 8) by a flexible tube of plastic 50 having overlapping ends 51, 52. To assure a snug fit while enabling easy assembly, the tubing 50 may be of the "shrink" type.

A further alternative spring construction is shown in FIG. 9 in which corresponding parts carry corresponding reference numerals with addition of subscript "a". In this version the spring elements 41a, 42a are separate from one another and the ends are kept in register to provide hinge joints 43a, 44a, by short lengths of tubing 50a. Or the spring elements may be totally enclosed. It is characteristic of the invention in all of its versions that the spring in its unstressed state has greater curvature than that which it will have at the end of the fill cycle, in other words, the unstressed spring dimension is greater than the thickness of the filled bag, so that, as the end of the fill cycle approaches, the spring will still be drawing an appreciable vacuum. Thus the spring 40a (FIG. 9) will preferably have an unstressed configuration approximating a circle as indicated at 40a'.

It is one of the features of the invention that the bowing of the reinforcing sheets 31, 32 into bowed or arch shape rigidifies the reinforcing sheets so that adequate reinforcing effect in both longitudinal and transverse directions is achieved using sheets of only limited thickness and bending modulus. In a typical case ordinary transparent acetate may be employed for reinforcement as thin as 10 mils. Because of the strength inherent in arched reinforcement, it suffices to employ two springs 40 at spaced points along the axis, and, indeed, it is possible to obtain a practical construction using slightly thicker reinforcing material with a single centrally located spring. Or, if desired, more than two springs may be employed without departing from the invention; for example, a pattern of thin pre-stressed spring wires (not shown) may be used, embedded in the reinforcing sheets and extending therein in parallel relation substantially from one edge to the other. Or, if desired, and without departing from the present invention, the reinforcing members 31, 32 may themselves be formed of relatively stiff yet flexible sheet material capable of acquiring pre-stress, making the use of auxiliary springs for this purpose unnecessary. Thus the members 31, 32 may be formed of thin spring metal, pre-stressed into outwardly bowed configuration, but because of visibility considerations the material of members 31, 32 should preferably be transparent, as discussed.

It is found that employing a bag which is initially of flat envelope shape, with the walls thereof being reinforced for outward bowing from a central axis, greatly improved vacuum characteristics are obtained. As contrasted with conventional vacuum drainage devices, in which the degree of vacuum tends to fall off rapidly as a function of flow, the vacuum in the present device is sustained at a high level over the fill cycle as indicated approximately in FIG. 11. It is one of the further distinguishing features of the invention that the device starts sucking at substantially zero initial volume. This not only enables a higher vacuum to be drawn with a given amount of maximum spring force but improves volumetric utilization since, in the filled state, substantially the entire volume is occupied by fluid with a minimum of air "header". This is to be contrasted with a popular type of vacuum device which includes telescoping cups pressed outwardly by spring force and where the cups in the collapsed state, unless specially pre-evacuated, define a substantial volume of air thereby reducing the liquid capacity. It is to be noted that while the present device may be supplied pre-evacuated, this is not a necessary condition. There are two possible modes of usage: In one mode the assembly may be supplied sealed, evacuated to the flat condition and with the catheter clamped. After the catheter has been placed in the wound the clamp is removed to begin the drainage process. In the alternate mode the assembly may be packaged in such a way as to keep the walls of the bag physically collapsed for maximum compactness, but with the walls being allowed to expand under the influence of the springs prior to usage. In such mode, the catheter is placed in the wound and temporarily clamped, the stopper 23 is temporarily removed permitting the device to be pressed flat with ordinary palm-applied force F (FIG. 4). The stopper is then replaced and the catheter unclamped to initiate drainage.

While it is preferred to arcuately cut out or "relieve" the reinforcing sheets at the ends to insure that there is a sufficient loose portion of the bag at the end edges 16, 17 to accommodate bowing separation, the reinforcing sheets 31, 32 may, if desired, be straight-ended and the necessary freedom achieved by extending the end edges of the bag arcuately outward.

The reinforcing sheets 31, 32 will normally be positioned inside the bag, between the spring and the wall of the bag, but it is not essential to do this in order to practice the invention, and the reinforcing sheets may be located outside of, and bonded to, the walls of the bag in a workable modification. Indeed, the invention may be practiced using less than a complete bag if desired: In such modification the sleeve 30, which provides the reinforcing sheets 31, 32 may be made of tubular stock, without the illustrated overlap, the bag "ends" 16, 17 may be thermally bonded to the ends of the sleeve. Such information is provided simply to assist the user in understanding the invention, and the preferred form of the invention will be understood to be that disclosed in FIG. 1 and associated figures.

While plastic is set forth as the preferred material for the bag 11 because of considerations of transparency, low cost, and ease of fabrication, including heat sealing, it will be understood that the term "plastic" is intended to include possible plastic subtitutes; for example, rubber might be employed for the bag without departing from the invention.

I claim:

1. A vacuum bag assembly for wound drainage comprising, in combination, an outer bag of thin flexible plastic in the form of an initially flat sealed envelope having opposed walls with parallel side edges defining a central axis as well as end edges, the edges being sealed, a sealed catheter connection providing communication to the space within the bag, the bag including first and second springs spaced along the axis, each spring being in the form of a pair of leaf spring elements lying back-to-back with their ends in register with one another and extending from one side edge of the bag to the other, the leaf spring elements being prestressed for bowing mutually outwardly in lenticular relation away from the central axis, the walls of the bag having reinforcement in the form of a flat sleeve formed of relatively stiff flexible sheets interposed between the springs and the walls of the bag so that upon bowing of the springs the walls of the bag are bowed outwardly uniformly over the major portion of the length thereof into a distended pillow of lenticular cross section for development of vacuum at the catheter connection.

2. A vacuum bag assembly for wound drainage comprising, in combination, an outer bag in the form of an initially flat sealed envelope of thin flexible plastic having opposed walls with parallel side edges defining a central axis between them as well as end edges, a catheter providing communication to the space within the bag, a flat sleeve formed of sheets of stiff but flexible plastic lying adjacent the inside surfaces of the respective walls for reinforcing the same, the sheets of stiff plastic extending substantially to the side edges of the walls but being inwardly offset from the end edges leaving the ends of the bag loose to accommodate outward bowing of the sheets, and at least one spring interposed between the sheets and prestressed outwardly for bowing the sheets and hence the walls of the bag mutually outwardly from the axis into a distended pillow of lenticular cross section for development of vacuum at the catheter connection.

3. The combination as claimed in claim 2 in which the bag and reinforcing sheets are both made of transparent plastic for visual monitoring of the drained liquid.

4. The combination as claimed in claim 2 in which the catheter is integral with the bag assembly and is in the form of a soft plastic tube sealed into one of the end edges.

5. The combination as claimed in claim 4 in which an auxiliary stoppered vent tube is sealed to the bag for initial venting of air and for emptying the contents of the bag.

6. The combination as claimed in claim 2 in which the inward offset of the reinforcing sheets is in the form of an arcuate relief at each end of the sheet.

7. The combination as claimed in claim 2 in which the spring elements in their unstressed state have a greater curvature than that which they have at the end of the fill cycle, so that appreciable vacuum is maintained right up until the end of the fill cycle.

8. A vacuum bag assembly for wound drainage comprising, in combination, an outer bag in the form of an initially flat envelope of thin flexible plastic having opposed walls with parallel side edges defining a central axis between them as well as end edges, the edges being sealed, a sealed catheter connection providing communication to the space within the bag, the walls having in face-to-face contact therewith reinforcing sheets of relatively stiff resilient material extending substantially to the side edges but offset inwardly of the end edges leaving the ends of the bag loose to accommodate outward bowing of the sheets, at least one spring in the bag in the form of a pair of leaf spring elements lying in opposed relation with their ends in register with one another, the spring elements being pre-stressed for bowing mutually outwardly away from the central axis, thereby pressing the walls of the bag outwardly into a distended pillow of lenticular cross section for development of vacuum within the bag, the spring elements comprising a spring being totally enclosed in a tubing of plastic, the tubing being dimensioned to confine the spring elements to define hinge connections at the adjacent ends thereof.

* * * * *